(12) United States Patent
Kaplan et al.

(10) Patent No.: US 6,354,993 B1
(45) Date of Patent: Mar. 12, 2002

(54) RIGID INTUBATING LARYNGOSCOPE WITH INTERCHANGEABLE BLADE AND VIDEO DISPLAY

(75) Inventors: Marshall B. Kaplan, Beverly Hills; George Berci, Los Angeles, both of CA (US); James P. Barry, Charlton, MA (US)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/337,626

(22) Filed: Jun. 21, 1999

(51) Int. Cl.[7] ............................................. A61B 1/267
(52) U.S. Cl. ...................................... 600/188; 600/199
(58) Field of Search ................................ 600/188, 199, 600/185, 120

(56) References Cited

U.S. PATENT DOCUMENTS

| | | | | |
|---|---|---|---|---|
| 3,986,854 A | * | 10/1976 | Scrivo et al. | 600/198 |
| 4,565,187 A | * | 1/1986 | Soloay | 600/199 |
| 5,261,392 A | * | 11/1993 | Wu | 600/188 |
| 5,751,340 A | * | 5/1998 | Strobl et al. | 348/65 |
| 5,827,178 A | * | 10/1998 | Berall | 600/188 |
| 6,123,666 A | * | 9/2000 | Wrenn et al. | 600/188 |

* cited by examiner

*Primary Examiner*—John Mulcahy
(74) *Attorney, Agent, or Firm*—St. Onge Steward Johnston & Reens LLC

(57) ABSTRACT

An intubating laryngoscope providing ready interchangeability of blades and a magnifiable video display for use in efficiently positioning an endotracheal tube through the vocal cords into the trachea and teaching the procedure.

19 Claims, 3 Drawing Sheets

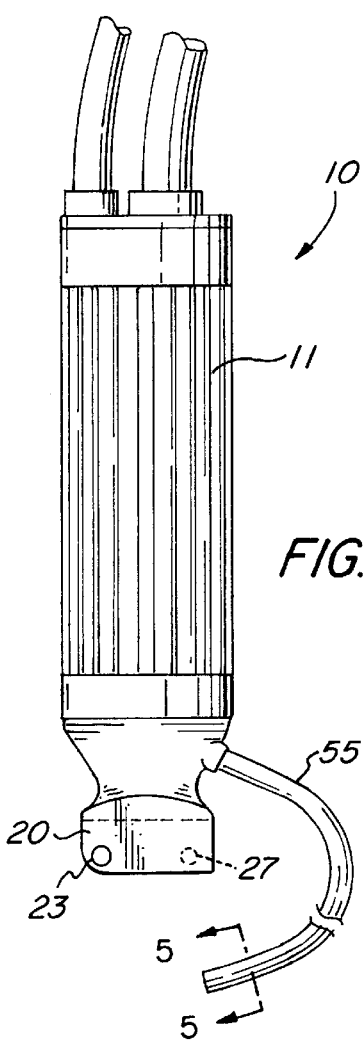
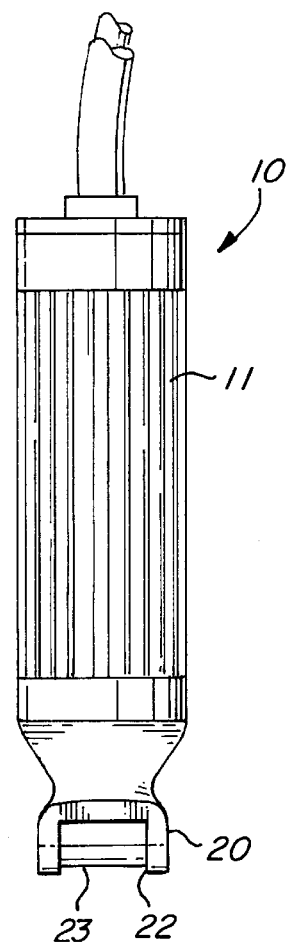
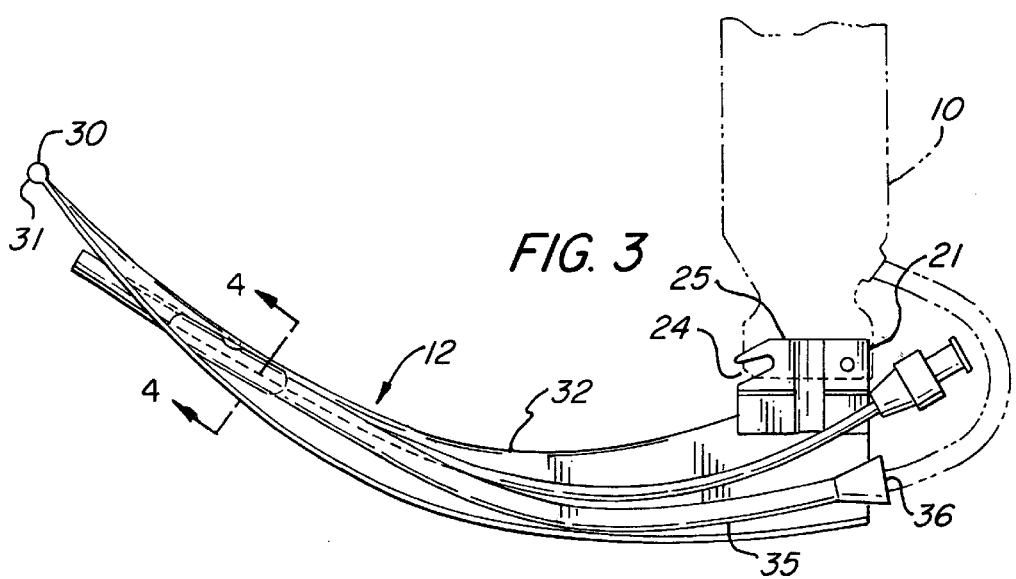

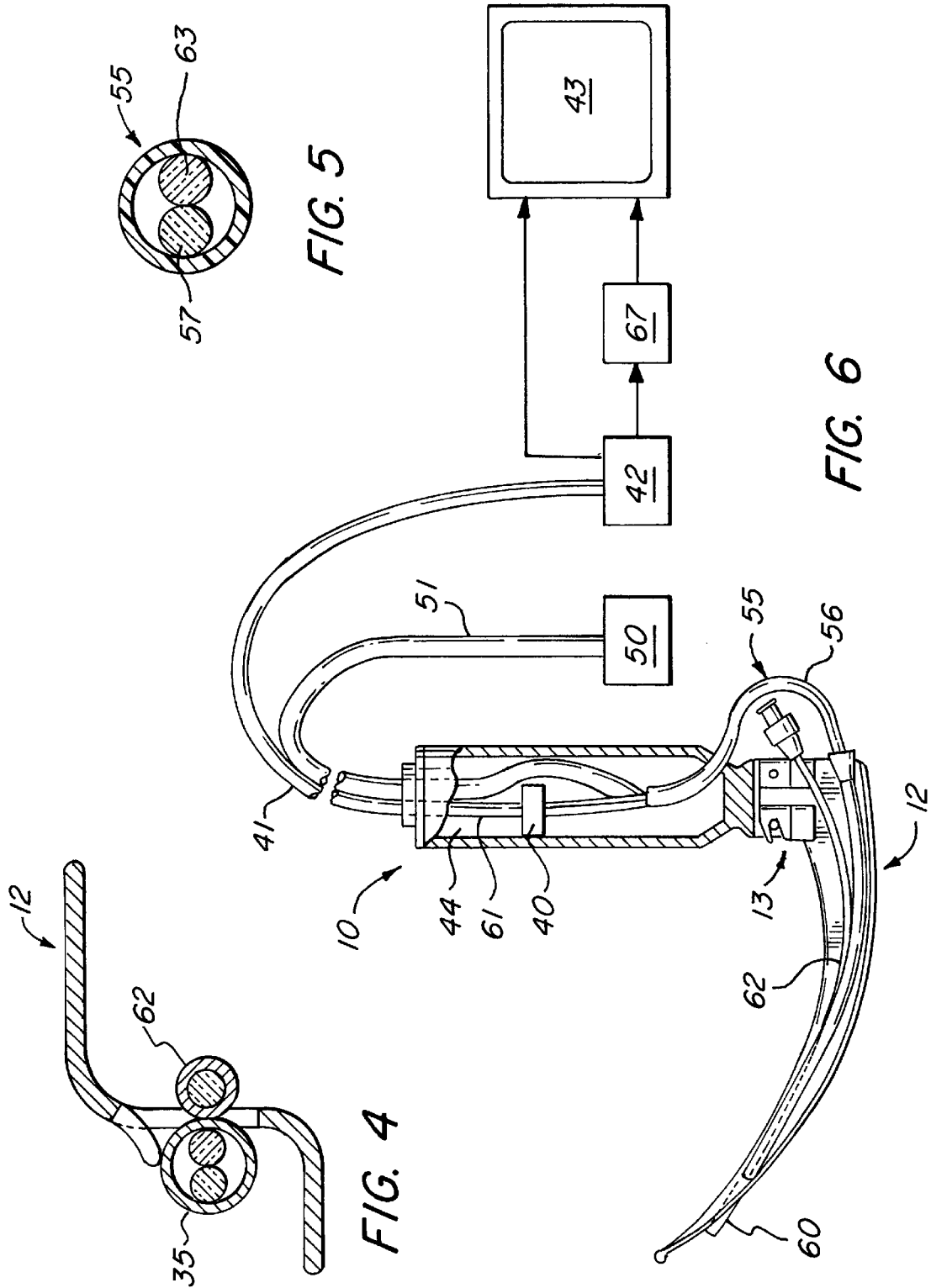

RIGID INTUBATING LARYNGOSCOPE WITH INTERCHANGEABLE BLADE AND VIDEO DISPLAY

FIELD OF THE INVENTION

An intubating laryngoscope providing ready interchangeability of blades and a magnifiable video display for use in efficiently positioning an endotracheal tube through the vocal cords into the trachea and teaching the procedure.

BACKGROUND OF THE INVENTION

In the United States approximately 20–22 million patients are operated on in general surgery and gynecology each year. Of these, about half or more require general anaesthesia in which the patient's breathing functions are temporarily disabled. Ventilation is supplied to the patient by the anesthesiologist during the procedure.

Ventilation is provided through an endotracheal tube. This tube is inserted into the trachea, and it is closed against the wall of the trachea by an inflatable cuff. The insertion of this tube involves risks that the anesthesiologist seeks to avoid or at least minimize. It is estimated that between one in 6,000 to one in 8,000 general anaesthesia procedures result in death. There are of course many causes but of these it is estimated that about one third of them are caused by the intubation procedure.

The principal problems the anesthesiologist encounters are the remoteness of the location where the tube is to go, the consequent restriction of view as the tube is inserted, variations and anomalies in the anatomy of the patients, an uncomfortable and unnatural position for the anesthesiologist, the potential need to change blades, and the necessity for rapid intubation.

It should be remembered that when the tube is to be inserted, the patient is asleep, and when he has been paralyzed for the procedure he is not breathing and the ventilator is not yet in operation. This gives the anesthesiologist only about two minutes in which to intubate the patient, inflate the cuff, and start ventilation. If he is delayed by the need to change blades of conventional instruments or by clumsiness of the instrument, he must stop, apply a mask, supply oxygen for a time through the mask, remove the mask, adjust medication if necessary, and then start over again. This delays the operation and extends the time under anaesthesia. Especially for elderly patients this is a very serious matter.

However, the need for speed cannot be permitted to expose the patient to greater risk. Severe damage can be done to the larynx and vocal cords, for example, by a tube which makes inappropriate contact with them. The object is to pass the tube smoothly where it will do no damage, namely directly between the vocal cords.

The direct visualization of the vocal cords through an open tube, which was the standard instrumentation for many years, gave only a limited and very unsatisfactory view of the region. It was like peering through a small keyhole into a dimly-lit region. Furthermore, it required the anesthesiologist to assume a most inconvenient posture while peering through the instrument, manipulating it with one hand, and pushing and turning the tube with the other. In practice it often required a "third hand" to manipulate a stylet which is often used. The literature and conversation in this field often refers to a third hand; (i.e. the need for an assistant).

With the advent of endoscopic equipment and small cameras, instrumentation has been improved to the extent that it can enable viewing of the cords and larynx on a screen. This in itself was a great advance in the field.

However, conventional instrumentation still fails to provide the anesthesiologist with an instrument which as to him is entirely standard and requires no special training, which provides an optimal video display of a full field of view that can be magnified, which can be fully utilized with only two hands without the need for an assistant and without stylets, in which blades can be changed quickly to account for the anatomical structure of the individual patient, and with which training can be done and records and teaching videos made.

It is an object of this invention to provide such an instrument with its stated advantages, especially those of accuracy, familiarity, rapidity, and efficiency.

BRIEF DESCRIPTION OF THE INVENTION

An instrument according to this invention includes a standard handle for the anesthesiologist to hold, a camera, a plurality of blades each having a configuration appropriate to a specific anatomical configuration, and a separable hinge type joinder having a portion on the handle and on each blade, the handle and the blades together forming a standard configuration familiar to all anesthesiologists trained in this procedure.

According to a feature of this invention, a cable guide tube extends along each said blade from a location adjacent to said joinder to a location near the tip of the blade. A flexible cable extends freely from the handle. It is inserted into the cable guide tube when the blade is attached to the handle. It is correctly positioned where the joinder is closed.

The cable itself conducts light to illuminate the field ahead of the tip of the blade. The cable also includes means to convey an image or data respective to an image of the region. When the camera is in the handle, the means in the cable is a coherent fiber optic bundle. When the camera is placed at the end of the cable, the means is a conductive lead.

In either arrangement, image bearing means and illumination means are carried by the cable respectively to obtain an image of it and to illuminate the region.

The light source may be a conventional battery and light bulb arrangement carried in the handle, or according to a preferred feature of the invention it may be a separate light source connected to the handle by a light-transmitting fiber optic bundle. With the use of this bundle, which may pass over the shoulder or to the side of the anesthesiologist, there is no interference with his movements or with the free advancement of the endotracheal tube.

The video display receives the image signal from the camera through a lead that extends from the handle. When an external light source is used, its fiber optic bundle will also exit from the handle. The lead and the bundle can conveniently exit from the back of the handle, and pass over or beside the shoulder of the anesthesiologist.

The above and other features of this invention will be fully understood from the following detailed description and the accompanying drawings, in which:

BRIEF DESCRIPTION OF THE DRAWINGS

FIG. 1 is aside view of a handle according to this invention;

FIG. 2 is a left hand view of FIG. 1;

FIG. 3 is a side view of a blade useful in this invention;

FIG. 4 is a cross-section taken at line 4—4 in FIG. 3;

FIG. 5 is a cross-section taken at line 5—5 in FIG. 1;

FIG. 6 is a side view, partly in schematic and partly in cross-section showing the system of the invention;

DETAILED DESCRIPTION OF THE INVENTION

An intubating laryngoscope 10 according to this invention is shown in FIG. 1. This, and all embodiments of the invention, includes a handle 11, which customarily is cylindrical with a knurled outer surface for a secure grip. It is shown in FIG. 6 detachably joined to a curved blade 12 by a hinge-type joinder 13.

Figure 7:
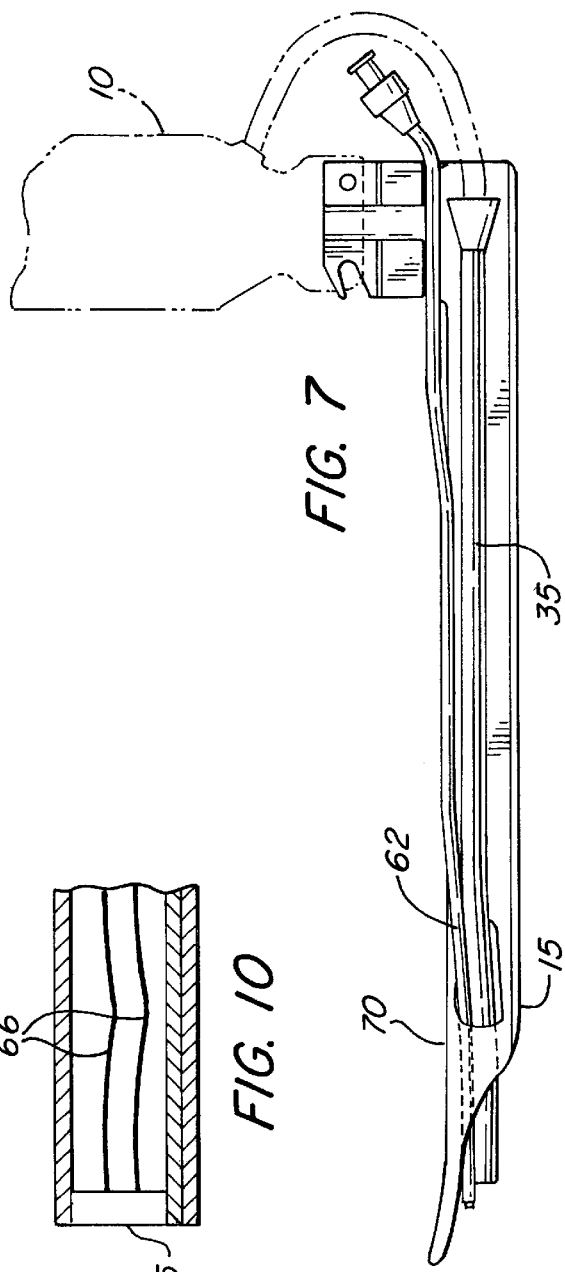
FIG. 7 is a side view of another useful blade.

The blade 12 illustrated in FIGS. 3 and 5 is a curved blade which is used to elevate the tongue in some circumstances. It is the well-known McIntosh blade. A different blade 15 for a different anatomical configuration is a straight blade adapted for use in other circumstances. It is shown in part in FIG. 7. This is the well-known Foregger-Magill blade. These are the two most common blades shapes. Their configuration is not a limitation on the invention. The configurations of this handle and these blades are completely conventional. They have been used by literally every anesthesiologist trained to intubate the trachea. An advantage of this invention is that it does not require any additional training or re-training of anesthesiologists who have used it or will in the future use it.

The hinge-type joinder 13 includes a pair of conventional hinge portions 20,21 respectively mounted to the lower end of the handle and of the proximal end of the blade. Portion 20 is a socket 22 having a cross-bar 23. Portion 21 has a hook 24 in a block 25 that fits in the socket. The hook engages the rod, and the handle is rotated 90 degrees so that the blade will be rigidly held to the handle. This is a common hinge-type joinder used in this type of instrumentation and is useful for all blade forms, of which the two illustrated forms are merely examples. A ball detent 27 releasably retains the portions together and erect in the assembled configuration. The assembled instrument is rigid during the procedure.

Curved blade 12 has a distal end 30 which may be smoothed by a bulb-like edge 31. It has a curved top surface 32 extending from the distal end toward the proximal end. This surface is used to elevate the tongue and permit the visualization of the vocal cords beneath it.

Blade 12 additionally includes a cable guide tube 35. At its proximal end it has an enlarged funnel-like entry portion 36. The guide tube is fixed to the blade and terminates near the distal end of the blade for reasons which will be disclosed. The entry portion 36 terminates near the joinder.

The handle is provided with means for obtaining an image of the field located beyond the tip of the blade, and for providing light to that field. In the presently preferred embodiment, a camera 40 (FIG. 6) is mounted with camera lens in the chamber 44 inside the handle.

A cable 41 to conduct the image data from the camera and in some embodiments brings illuminating light to the handle, exits from the top of the handle. It is connected to a video set 42 which provides data for an image on a video screen 43 for observation by the anesthesiologist.

The video set also provides for magnification of the image. It is important that a true video screen be used rather than a PC screen. This is because a PC screen can effectively be viewed no more than a few degrees off of the perpendicular to the screen, and thereby constitutes a limitation on the freedom of the anesthesiologist's head movement. In addition, their resolution and brilliance are insufficient for effective viewing by a very busy anesthesiologist.

In the preferred embodiment of the invention, light for illumination is obtained from a separate light source 50 that can be placed in any convenient nearby location. A fiber optic bundle 51 extends from the light source to the handle, conveniently in cable 41. Both enter chamber 44 in the handle where the camera is located.

As a feature of this invention, a flexible cable 55 exists freely from the handle near its lower end. This cable is intended to be inserted into the guide tube when the blade is joined to the handle. Its free end can quickly and easily be inserted into the guide tube and advanced into it so that its free end is exposed to and directed toward the region below and ahead of the distal end of the blade. A slack bend 56 in the cable enables the cable to bend when the handle is pivoted relative to the blade in its hinge-like movement. Similar provisions are incorporated in all blades used in the invention.

The actual construction and content of cable 55 depends on the arrangement of the camera and of the light source. In the preferred embodiment shown in FIG. 6, camera 40, customarily a CCD chip, is mounted to the handle inside chamber 44. Then the cable will include a fiber optic bundle 57 of coherent strands which extends from an objective lens 60 at its distal end to the camera. This will convey an image to the camera.

A lead 61 from the camera (conveniently housed in cable 41) carries the data to a video set 42, which provides data for an image on a video screen 43, for observation by the anesthesiologist. This lead exits from the end of the handle as part of cable 41 and passes over the shoulder of the anesthesiologist or to his side. It is out of his way.

For illumination purposes a second fiber optic bundle 63 is provided in cable 55. It is optically coupled to bundle 51 and is in effect a continuation of it. Bundle 63 need not be coherent, because it does not transmit an image- it transmits only light, The light is directed from its distal end to the field of view.

It will now be seen that joining the blade to the handle and completing the assembly of light and image means is a swift process. The end of cable 55 is merely shoved into the funnel-like open end 36 of guide tube 35, and the portions of the joinder are engaged. The handle is then rotated, and the instrument is ready for use. Removal is quick-merely rotate the handle to release the blade, and pull the handle away from the blade. Removal and replacement are very simple.

If desired, an oxygen-carrying conduit 62 (FIG. 4) may be attached to the blade, discharging a slow stream of oxygen across the objective lens to prevent its fogging-up.

Blade 15 (FIG. 2) differs from blade 12 only by its shape. It has a straight upper surface 70 instead of a curved surface for use when such a surface is preferred for lifting the tongue of the individual patent. In all cases the objective is to lift the tongue to permit visualization of the vocal cords and to enable the endotracheal tube to be accurately placed without harming surrounding tissue in the process.

Instead of the camera and illumination arrangements already described, there are other alternatives which can be used in any combination.

For example, instead of employing a separate light source, a battery ad light bulb may be contained in the handle, and the light from this bulb focused onto bundle 63. A disadvantage of this arrangement is the increase in size and weight of the handle because of the contained battery. Still, this eliminates the need for a fiber optic bundle from a light source, and also eliminates the separate light source itself. The principal advantage of the use of a separate light source is that the handle can be made thinner, and the instrument made lighter.

Figure 10:
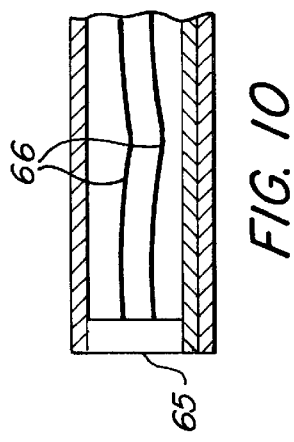
FIG. 10 is an axial section partly in schematic notation showing an alternate camera arrangement.

In the preferred embodiment the camera will be placed in the handle as already described. However, it is equally feasible to place a camera 65 at the end of the cable as shown in FIG. 10. In this situation the cable 55 will carry, instead of a coherent fiber optic, leads 66 conveying the camera data output from the camera to the handle, and through the handle to cable 41 and thence to the video set.

Notice that in every situation the cable from the handle to the blade is flexible, passes into the guide, and is thereby accurately placed for use. When the blade is separated from the handle, the cable is simply pulled out of the tube and accompanies the handle.

The display may be improved by eliminating the raster pattern from the image by use of apparatus 67 shown in U.S. Pat. No. 5,751,340, which will be interposed between the set and the display. This patent is made a part hereof by reference in its entirety for its showing of a useful system for this purpose. Its use is optional.

Figure 9:
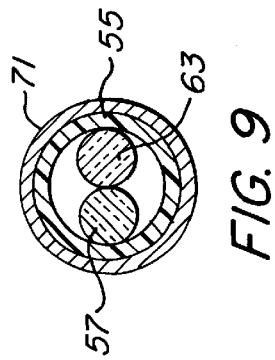
FIG. 9 is a cross-section taken at line 9—9 in FIG. 8.
Figure 8:
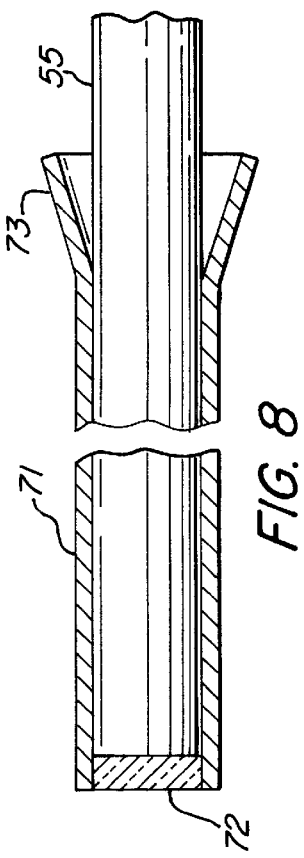
FIG. 8 is an axial cross-section of an optional cable and guide assembly.

All existing conventional blades which provide illumination include a tube which hold illumination means in place, for example fiber optic bundles. The guide tube of this invention may be directly substituted for them. There is a useful optional improvement shown in FIGS. 8 and 9. In this embodiment, instead of a permanently-installed guide tube, a clip such as clip 70 (FIG. 3) is provided. Then a plastic tube 71 with an acrylic window 72 and a funnel-like guide 73 is clipped in place as in FIG. 3. The guide tube will be pre-sterilized. Bundle 55 is placed in it. It need not be sterilized, which is an advantage. The plastic guide tube will be discarded after the procedure.

A vivid display is observable from a wide angle, which facilitates training. The trainer can easily observe the trained student and his work, and guide him. Without such a display, the instructor cannot see what the trainee is doing. With a magnified video view, both the student and the trainer have a simultaneous view of what the trainee is doing.

This system lends itself to recordation for legal purposes, as well as providing a library for training students while they are not under the direct supervision of the instructor. In the United States there are about 150 teaching institutions, and about 30,000 anesthesiologists. Library-type video tapes are a particularly valuable means to reach the very large number of anesthesiologists who are years away from their student days, and who have little opportunity for direct-participation in re-education for such a fundamental procedure.

This invention in not to be limited to the embodiments shown in the drawings and described in the description, which are given by way of example and not of limitation, but only in accordance with the scope of the appended claims.

We claim:

1. An intubating laryngoscope system providing for ready interchange of blades, for video display, and for convenience in use comprising:
    a handle;
    a blade having a proximal end, and a distal end;
    a hinge-like joinder detachably joining said handle and said blade, such that in a released configuration said handle and said blade are separable, the handle and blade being rigidly attached to one another in an engaged orientation;
    a flexible cable extending from said handle having an end fixed to the handle, and a free end;
    a guide tube attached to said blade, extending from near the proximal end of the blade toward its distal end, said guide tube adapted to receive the free end of said flexible cable, and including an enlarged funnel-like entry portion to facilitate the entry of the free end of said flexible cable into said guide tube, said guide tube having an opening at its distal end with a window to facilitate illumination of the area ahead of the blade and to permit receipt of images by an image sensor;
    wherein said flexible cable is insertable and removable from said guide tube, such that a plurality of blades may be interchanged with said handle and said flexible cable;
    a camera operatively connected to said flexible cable;
    a light source operatively connected to said flexible cable;
    a light-transmitting fiber optic in said flexible cable;
    image-transmitting means in said flexible cable;
    a second cable extending from said handle;
    a video receiver connected to said second cable receptive to signals from said camera; and
    a video screen receptive to said video received to display images transmitted from said camera.

2. A system according to claim 1 in which said camera is disposed in a chamber in a said handle, and said flexible cable comprises a coherent fiber optic bundle having one end exposed to a field of view and a second end exposed to said camera.

3. A system according to claim 1 in which said light source is separate from the handle, and in which said light-transmitting fiber optic is adapted to receive light from said light source to be transmitted to the field of view.

4. A system according to claim 3 in which said camera is disposed in a chamber in said handle, and said flexible cable includes a coherent fiber optic bundle having one end exposed to a field of view and a second end exposed to said camera.

5. A system according to claim 1 in which said camera is mounted to the distal end of the flexible cable, and the image-transmitting means is a lead which conveys image data through said handle to said video receiver.

6. A system according to claim 1 in which said light source is a battery and bulb combination in said handle to provide light to said light-transmitting means.

7. A system according to claim 1 in which said guide tube has a closed distal end with an optically clear and transparent window at said distal end, and a wall extending to said entry portion, said wall and said window being imperforate and sterilizeable, whereby a non-sterile said flexible cable can be inserted into said guide tube, and the guide tube disposed of after use without need to sterilize the flexible cable before its next use.

8. A system according to claim 1 in which a device to remove the geometric pattern from the signal to the video screen receives and processes the image signal from the camera.

9. A laryngoscope system according to claim 1 in which a conduit mounted to the blade with an exit opening near the distal end of the flexible cable is adapted to discharge a stream of oxygen adjacent to the distal end of the guide tube.

10. A system according to claim 1 wherein said guide tube is provided with an acrylic window in said opening at the distal end of said guide tube.

11. A system according to claim 1 wherein said guide tube is pre-sterilized and can be temporarily clipped onto the blade for use, after which it can be removed and discarded.

12. An intubating laryngoscope system enabling ready interchange of blades, video display, and convenient use, comprising:

a handle;

a blade having a proximal end, and a distal end;

a hinge-like joinder detachably joining said handle and said blade, such that in a released configuration said handle and said blade are separable, the handle and blade being rigidly attached to one another in the engaged orientation;

a flexible cable extending from said handle having an end fixed to the handle, and a free end;

a guide tube attached to said blade, extending from near the proximal end of the blade toward its distal end, said guide tube adapted to receive the free end of said flexible cable, and including an enlarged funnel-like entry portion to facilitate the entry of the free end of said flexible cable into said guide tube, said guide tube having an opening at its distal end with a window to facilitate illumination of the area ahead of the blade and to permit receipt of images by an image sensor;

wherein said flexible cable is insertable and removable from said guide tube, such that a plurality of blades may be interchanged with said handle and said flexible cable;

a camera operatively connected to said flexible cable;

a light source operatively connected to said flexible cable a light-transmitting fiber optic in said flexible cable;

image-transmitting means in said flexible cable; and a second cable extending from said handle; and said second cable being adapted to be connected to a video receiver which is receptive to signals from said camera.

13. A laryngoscope according to claim 12 in which said camera is disposed in a chamber in said handle, and said flexible cable comprises a coherent fiber optic bundle having one end exposed to a field of view and a second end exposed to said camera.

14. A laryngoscope according to claim 12 in which said light transmitting fiber optic in said flexible cable is adapted to receive light from a separate light source to be transmitted to the field of view.

15. A laryngoscope according to claim 14 in which said camera is disposed in a chamber in said handle and said flexible cable includes a coherent fiber optic bundle having one end exposed to a field of view and a second end exposed to said camera.

16. A laryngoscope according to claim 12 in which said camera is mounted to the distal end of the flexible cable, and the image-transmitting means is a lead from said camera extending through said handle for conveying image data through said handle to a video receiver.

17. A laryngoscope according to claim 12 in which said light source is a battery and bulb combination in said handle, to provide light to said light-transmitting fiber optic.

18. A laryngoscope according to claim 12 in which said guide tube has a closed distal end with an optically clear and transparent window at said distal end, and a wall extending to said entry portion, said wall and said window being imperforate and sterilizeable, whereby a non-sterile said flexible cable can be inserted into said guide tube, and the guide tube disposed of after use without need to sterilize the flexible cable before its next use.

19. A laryngoscope according to claim 12 in which a conduit mounted to the blade with an exit opening near the distal end of the flexible cable is adapted to discharge a stream of oxygen adjacent to the distal end of the guide tube.

* * * * *